United States Patent
Cowan et al.

(10) Patent No.: US 11,071,469 B2
(45) Date of Patent: Jul. 27, 2021

(54) MAGNETIC RESONANCE METHOD AND APPARATUS FOR DETERMINING A CHARACTERISTIC OF AN ORGAN

(71) Applicant: Siemens Healthcare GmbH, Erlangen (DE)

(72) Inventors: Brett Cowan, Auckland (NZ); Eric Schrauben, Auckland (NZ); Alistair Young, Auckland (NZ); Andreas Greiser, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 384 days.

(21) Appl. No.: 15/672,590

(22) Filed: Aug. 9, 2017

(65) Prior Publication Data

US 2018/0042497 A1     Feb. 15, 2018

(30) Foreign Application Priority Data

Aug. 9, 2016   (DE) .......................... 102016214775.7

(51) Int. Cl.
*A61B 5/026* (2006.01)
*G01R 33/563* (2006.01)
(Continued)

(52) U.S. Cl.
CPC .......... *A61B 5/0263* (2013.01); *A61B 5/0044* (2013.01); *A61B 5/029* (2013.01); *G01R 33/5608* (2013.01); *G01R 33/5613* (2013.01); *G01R 33/56308* (2013.01); *G01R 33/56333* (2013.01); *G06T 3/0081* (2013.01);
(Continued)

(58) Field of Classification Search
CPC ..... A61B 5/0263; A61B 5/029; A61B 5/0044; G06T 7/0016; G06T 3/0081; G06T 2210/41; G06T 2207/30048; G06T 2207/10088; G06T 11/008; G01R 33/56308; G01R 33/5613; G01R 33/5608; G01R 33/56333
See application file for complete search history.

(56) References Cited

U.S. PATENT DOCUMENTS 5,274,549 A * 12/1993 Almasi ............... A61B 5/02755
382/128
6,171,241 B1 * 1/2001 McVeigh ............... A61B 5/055
600/410
(Continued)

OTHER PUBLICATIONS

Qian, Zhen, et al. "A novel tag removal technique for tagged cardiac MRI and its applications."; 2007 4th IEEE International Symposium on Biomedical Imaging: From Nano to Macro. IEEE, 2007. (Year: 2007).*
(Continued)

*Primary Examiner* — Sean D Mattson
(74) *Attorney, Agent, or Firm* — Schiff Hardin LLP (57) ABSTRACT

In a magnetic resonance method and apparatus for determining a characteristic of an organ, a magnetic resonance sequence is executed in order to acquire temporally resolved magnetic resonance data pertaining to the organ. The magnetic resonance sequence includes at least one tagging module, which generates a sub-visual tag of the magnetic resonance data. The characteristic of the organ is determined in a processor using the sub-visual tag.

14 Claims, 3 Drawing Sheets

(51) Int. Cl.
  *A61B 5/00* (2006.01)
  *A61B 5/029* (2006.01)
  *G01R 33/56* (2006.01)
  *G01R 33/561* (2006.01)
  *G06T 3/00* (2006.01)
  *G06T 7/00* (2017.01)
  *G06T 11/00* (2006.01)

(52) U.S. Cl.
  CPC .......... *G06T 7/0016* (2013.01); *G06T 11/008* (2013.01); *G06T 2207/10088* (2013.01); *G06T 2207/30048* (2013.01); *G06T 2210/41* (2013.01)

(56) References Cited

U.S. PATENT DOCUMENTS

| | | | | |
|---|---|---|---|---|
| 6,757,423 | B1* | 6/2004 | Amini | G06T 7/246 382/128 |
| 2009/0281415 | A1* | 11/2009 | Cupps | A61B 5/055 600/410 |
| 2012/0045107 | A1* | 2/2012 | Matsuda | A61B 5/055 382/131 |
| 2013/0294669 | A1* | 11/2013 | El-Baz | G06T 7/42 382/131 |

OTHER PUBLICATIONS

Johnson, Thorsten RC, et al. "Myocardial tagging with steady state free precession techniques and semi-automatic postprocessing—impact on diagnostic value." European radiology 17.9 (2007): 2218-2224. (Year: 2007).*

Cowan et al.: "Letter to the Editor", in: JACC: Cardiovascular Imaging, (2015).

Markl et al.: "Balanced left Ventricular Maycardial SSFP-Taggihg at 1.5T and 3T"; Magnetic Resonance in Medicine, vol. 60, pp. 631-639. (2008).

Augustine et al.: "Global and regional left ventricular myocardial deformation measures by magnetic resonance feature tracking in healthy volunteers: comparison with tagging and relevance of gender", in: Journal of Cardiovascular Magnetic Resonance, vol. 15, No. 8, pp. 1-10, (2016).

Li et al.: "GPU Accelerated Non-rigid Registration for the Evaluation of Cardiac Function",: MICCAI 2008, Part II, pp. 880-887; (2008).

Zwanenburg, et al.: "Steady-State Free Precession With Myocardial Tagging: CSPAMM in a Single Breathhold",: Magnetic Resonance in Medicine, vol. 49, pp. 722-730, (2003).

Osman, et al.: "Imaging Heart Motion Using Harmonic Phase MRI", in: IEEE Transactions on Medical Imaging, vol. 19, No. 3, , pp. 186-202 (2000).

Zerhouni, et al: "Human Heart: Tagging With MR Imaging—A Method for Noninvasive Assessment of Myocardial Motion"; Cardiac Radiology, vol. 169, No. 1, pp. 59-63 (1988).

Axel et al. "Heart Wall Motion: Improved Method of Spatial Modulation of Magnetization for MR Imaging" Radiology, vol. 172: pp. 349-350 (1989).

* cited by examiner

MAGNETIC RESONANCE METHOD AND APPARATUS FOR DETERMINING A CHARACTERISTIC OF AN ORGAN

BACKGROUND OF THE INVENTION

Field of the Invention

The invention concerns a method, a magnetic resonance apparatus and a non-transitory, computer-readable data storage carrier for determining a characteristic of an organ by magnetic resonance.

Description of the Prior Art

In magnetic resonance imaging, the body of a subject to be examined using a magnetic resonance scanner, in particular a patient, is exposed to a relatively high basic magnetic field of for example, 1.5 or 3 or 7 Tesla, generated by a basic field magnet. In addition, gradient fields are created with the use of a gradient coil arrangement. Then, using appropriate antennas, radio-frequency pulses, such as excitation pulses, are radiated by a radio-frequency antenna, which leads to the nuclear spins of certain atoms that have been resonantly excited by these radio-frequency pulses being tilted by a defined flip angle with respect to the magnetic field lines of the basic magnetic field. During the relaxation of these nuclear spins, radio-frequency signals referred to as magnetic resonance signals are emitted, and are received by appropriate radio-frequency antennas and then further processed. The raw data acquired in this manner are used to reconstruct the desired image data.

A specific scan therefore requires the transmission of a specific magnetic resonance sequence composed of a succession of radio-frequency pulses, such as excitation pulses and refocusing pulses, together with gradient fields that are activated in time coordination therewith, in different spatial directions along respective gradient axes. Readout windows, timed to coincide with the gradient fields, specify the time periods in which the magnetic resonance signals that have been induced, that is, the magnetic resonance data, can be acquired.

The image data are spatially resolved and represent the reconstructed magnetic resonance signals. The image data are typically restricted to a specific spatial region of the examination subject, the region of examination. Depending on the magnetic resonance sequence and the reconstruction method used, the image data have different contrasts so as to depict the anatomy. Image data can likewise be acquired in a time series so as to not only represent the two or three spatial dimensions, but also to show temporal changes in the examination region.

With such a time series, a function of an organ located in the examination region can be characterized visually using the image data. For example, the time series of image data for a heart can be used to determine the diastolic and the systolic volume. For this purpose, the image data will preferably have a particularly strong contrast between the vascular wall and the blood. If a different function of the organ is to be determined, then a different contrast can be helpful.

In magnetic resonance tomography, for determining a periodic deformation of an organ, tagging methods are known, for example, in Zerhouni et al., "Human heart: tagging with MR imaging—a method for noninvasive assessment of myocardial motion", Radiology, 169(1), 59-63. Tagging methods generate a visible pattern in the examination region, which pattern undergoes deformation along with the organ. This deformation of the pattern can be shown with temporal resolution by a time series of image data. A deformation of the organ can be inferred on the basis of the deformation of the pattern. The tagging methods are typically based on gradient echo sequences.

SUMMARY OF THE INVENTION

An object of the invention is to provide a flexible method for determining a characteristic of an organ by operation of a magnetic resonance apparatus, i.e. the scanner thereof. A further object is to provide a magnetic resonance apparatus and a non-transitory, computer-readable data storage carrier that are designed to implement the method.

The method according to the invention for determining a characteristic of an organ by means of a magnetic resonance apparatus includes the following process steps. A magnetic resonance scanner is operated in order to execute a magnetic resonance sequence so as to acquire temporally resolved magnetic resonance data pertaining to the organ, the magnetic resonance sequence including at least one tagging module, which generates a sub-visual tag of the magnetic resonance data. The characteristic of the organ is determined by computer analysis using the sub-visual tag. The result of the computer analysis is made available in electronic form from the computer.

The execution of the magnetic resonance sequence generates a series of magnetic resonance data that is temporally resolved. Temporally resolved magnetic resonance data are preferably acquired sequentially. The magnetic resonance data that have been acquired are preferably assigned to a point in time during the execution of the sequence. The magnetic resonance data can be reconstructed into temporally resolved image data. The temporal resolution of the image data may differ from the temporal resolution of the magnetic resonance data.

If the organ is performing a periodic motion, it is advantageous to coordinate the execution of the magnetic resonance sequence with the periodic motion. The temporally resolved magnetic resonance data are preferably acquired so as to be able to reconstruct image data therefrom, which image data preferably depicts the organ at various phases within a period. The execution of the magnetic resonance sequence and the acquisition of the magnetic resonance data may extend over multiple periods in the motion of the organ.

The magnetic resonance sequence includes a tagging module, which typically includes a radio-frequency pulse and/or a gradient pulse. The tagging module is typically incorporated into the magnetic resonance sequence. The magnetic resonance sequence typically include a number of blocks. Each block typically has an excitation module in order to excite spins in the examination region and an encoding module for spatially encoding the spins excited in the examination region and to receive signals, i.e. the magnetic resonance data emitted by spins excited in the examination region. For example, in temporal terms, a tagging module can be executed before executing a block. Magnetic resonance data that are acquired using a magnetic resonance sequence that includes a tagging module are referred to as tagged magnetic resonance data. When tagged magnetic resonance data are reconstructed into image data, then the image data are referred to as tagged image data.

The tagging module preferably carries out a location-dependent modulation of the spins in the examination region. The location-dependent modulation can be referred to as tagging. The modulation typically influences the orientation of the spins during the acquisition of the magnetic resonance data and/or during the execution of the encoding module and consequently the magnetic resonance data and the intensity of the signal acquired. The location-dependent modulation of the spins typically effects a location-dependent modulation of the signal intensity in the tagged image data. The location-dependent modulation of the signal intensity may be referred to as a tagging pattern. The tagging pattern is preferably imprinted on the spins during the execution of the tagging modules. The spatial modulation generated by the tagging module typically moves with the organ in the examination region. If a motion, in particular a motion of the organ, occurs in the examination region between the execution of the tagging module and the acquisition of the magnetic resonance data and/or up to the execution of the encoding module, then this is typically reflected in the modulation of the tagged magnetic resonance data and in the tagged image data. If, in temporal terms, the spins undergo a spatial change between the execution of the tagging module and the acquisition of the MR signals, then the tagging pattern typically also undergoes a spatial change. The spatial change can be a deformation and/or a translation. If the tagging module were to be suppressed during the execution of the magnetic resonance sequence, then magnetic resonance data that can be reconstructed into image data would typically be acquired, which image data do not have any modulation generated by the tagging module.

In conventional tagging methods, such a modulation can be detected in the tagged image data. A pattern generated by the conventional location-dependent modulation of the spins typically appears in the tagged image data as a signal cancelation or an easily detectable signal reduction. In image data that have been acquired by a conventional tagging method, the tagging pattern typically dominates the contrast. The method according to the invention uses a tagging module that generates sub-visual tagging. The reconstruction of sub-visually tagged magnetic resonance data generates sub-visually tagged image data.

The tagging pattern is preferably not detectable to a trained observer in the sub-visually tagged image data.

The tagging pattern is preferably not visible in the sub-visually tagged image data in a display format of the image data. A trained observer, such as a radiologist, for example, can make a clinical diagnosis on the basis of the image data in the display format. The sub-visual tagging pattern preferably does not influence the clinical diagnosis. The display format is typically based on a contrast and/or a brightness and/or a windowing of the sub-visually tagged image data. The signal difference in the sub-visually tagged image data between a first pixel, which is located in the tagging pattern and/or the signal-generating spins of which have been modulated during the execution of the tagging module, and a second pixel, which does not undergo any modulation and/or the signal-generating spins of which have not been modulated during the execution of the tagging module, is preferably lower than 50% of the maximum signal difference in the image data. More preferably this difference is lower than 30%, and more preferably lower than 15% of the maximum signal difference in the image data. The maximum signal difference in the image data is the difference between the maximum signal and the minimum signal in the pixels included in the image data.

The image data are typically displayed to a user in gray-scale values. A scale with 256 different gray-scale values is preferably used. The value range for the scale used is preferably selected such that the image data are displayed in the display format. In particular, the range of values for the scale used for the image data is typically selected such that a clinical diagnosis can be made on the basis of the image data in that display format. The human eye typically can distinguish between from 60 to 80 different gray-scale values. Consequently, a user can typically distinguish only the gray-scale values for various pixels from one another when the gray-scale values are at least four values apart on the scale. The sub-visual tag generates a change in the signal intensity of a first pixel, which is located in the tagging pattern and/or the signal-generating spins of which have been modulated during the execution of the tagging module, preferably by less than 50 gray-scale values, typically by a maximum of 20 gray-scale values, preferably by a maximum of 10 gray-scale values, particularly preferably by a maximum of 5 gray-scale values.

On the basis of the sub-visually tagged magnetic resonance data, the characteristic of the organ is determined. It is possible for more than one characteristic of the organ to be determined. The characteristic of the organ is preferably determined due to a temporary change and/or evolution of the organ, which temporary change and/or evolution of the organ can be detected using the sub-visually tagged, temporally resolved magnetic resonance data. For example, the characteristic may include an outer shape of the organ and/or a change in the outer shape of the organ. The characteristic of the organ may include a translation of the spatial position of the organ and/or a deformation of the organ, such as a cardiac contraction, for example. The characteristic may include a change in components located in the organ and/or a rearrangement of components located in the organ. The changes mentioned preferably occur during the acquisition of the temporally resolved magnetic resonance data pertaining to the organ.

As noted, in order to determine the characteristic of the organ, the temporal change in the tagging pattern in the sub-visually tagged magnetic resonance data is analyzed in a computer. The tagging pattern can be extracted from the sub-visually tagged, temporally resolved magnetic resonance data using, for example, an evaluation algorithm. If the sub-visually tagged magnetic resonance data were to be reconstructed into image data, then a change in the signal intensity due to the slight deviations in the gray-scale values in the tagging pattern from the area surrounding the tagging pattern would not be detectable to the human eye. The evaluation algorithm is able to detect slight gray-scale differences that are not detectable to the human eye, such as differences of less than 5 gray-scale values, on a scale suitable for the display format, and thereby analyze the tagging pattern. The evaluation algorithm can be designed such that changes in the magnetic resonance data generated by the tagging module in the raw data can be detected. Changes in the tagging pattern are preferably detected in a spatially and temporally resolved manner. To this end, the magnetic resonance data are evaluated using registration methods. Alternatively or additionally, further image-processing methods can be used to determine the characteristic of the organ, such as a free-form deformation. Knowledge of the tagging that has been generated, such as the expected spatial modulation of the image data for at least one point in time and/or quantitative distances between regions of induced signal cancelation and/or signal reduction, can be considered when determining the characteristic of the organ in the free-form deformation. Such a procedure may be based, for example, on the HARP algorithm (Osman et al., "Imaging Heart Motion Using Harmonic Phase MRI", IEEE Trans Med Imaging, 19(3), 186-202).

An advantage of the method according to the invention for determining a characteristic of an organ is that the determination of the characteristic of the organ does not affect the diagnostic value of the magnetic resonance data. On the basis of the sub-visually tagged magnetic resonance data, both the characteristic of the organ can be determined and image data can be generated. With such data, the organ can be displayed in a clinical contrast with the image data not being influenced by the tag. The magnetic resonance sequence is typically designed such that the sub-visually tagged magnetic resonance data generated thereby represent, in the reconstruction of the tagged image data, the anatomy of the examination region with a clinically relevant contrast, such that any pathology present can be recognized. Consequently, the execution of the magnetic resonance sequence is sufficient to generate temporally resolved image data and to generate the magnetic resonance data for determining the characteristic of the organ. As a result, the method according to the invention allows a flexible determination of the characteristic of the organ, which can be combined for example, with further scans.

Image data acquired using a conventional tagging method are typically not suitable for determining a further function of the organ. Conventional tagging methods are typically time-intensive and typically can only be measured with a low temporal resolution. In the conventional method, the execution of two different magnetic resonance sequences is typically required for determining a characteristic of the organ, and for generating diagnostically relevant, temporally resolved image data. Consequently, in the method according to the invention, as compared with conventional methods, the entire scan time can be reduced and/or the comfort of patients increased and/or the cost-effectiveness of the magnetic resonance apparatus can be increased. In summary, with the method according to the invention, a characteristic of an organ can be determined by operation of a magnetic resonance apparatus in a flexible and precise manner. The more refined, that is, the higher-resolution, the tagging pattern is, the more precisely the characteristic of the organ can be determined. Since a sub-visual tagging pattern is used in the method according to the invention, the structure and/or resolution thereof can be selected individually without the diagnostic quality of the image data being affected.

In an embodiment of the method, the determination of the characteristic of the organ includes a reconstruction of the magnetic resonance data into image data, and an extraction of a modulation of the image data generated by sub-visual tagging.

Magnetic resonance data are typically in the frequency domain. The reconstruction thereof into image data is typically carried out by a Fourier transform. The reconstructed image data typically reflect a spatial signal distribution in pixels. The reconstructed image data are preferably temporally resolved and are preferably displayed in a time series. The course of the image data over time may be referred to as the fourth dimension. The sub-visually tagged image data embody a modulation of the tagging module that is not visible to the user. The tagging pattern is extracted according to this embodiment. The tagging pattern is typically a spatial signal distribution that, for example, has been imprinted on the spins in the form of a geometric structure by executing the magnetic resonance sequence at the time of execution of the tagging module. The tagging pattern that has been extracted can be provided as a spatial distribution. The tagging pattern is typically linked with the examination region, in particular with the organ, such that a deformation and/or translation of the organ and/or of further components included in the examination region are transferred to the tagging pattern. The tagging pattern is preferably extracted from the sub-visually tagged image data for various points of time in the fourth dimension. The tagging pattern typically varies in the fourth dimension.

For the extraction of the modulation, the individual pixels in the image data are preferably classified using minimization methods according to the following criteria:
  a first region, which is located in the tagging pattern and/or the signal-generating spins of which have been modulated during the execution of the tagging module,
  a second region, which does not undergo any modulation and/or the signal-generating spins of which have not been modulated during the running of the tagging module.

The pixels that have been classified are preferably combined in a binary image. The extraction of the modulation is preferably repeated for all the image data assigned to a point in time along the fourth dimension. On the basis of the temporal changes in the binary image and on the image data, the characteristic of the organ can be determined. For this purpose, the binary image is typically underpinned by and/or combined with the image data.

An advantage of this embodiment of the method is that, by the extraction of the modulation from the image data, the characteristic of the organ can be determined in a particularly precise manner. The procedure described for the extraction of the modulation for individual pixels is reproducible. Slight modulations, such as those that occur with sub-visual modulations, can be detected particularly well. The resulting binary image reproduces the modulation in a particularly precise manner.

In another embodiment of the method, the determination of the characteristic of the organ includes an elastic registration, based on the modulation that has been extracted. An elastic registration is carried out, preferably based on the modulation that has been extracted, particularly preferably based on the binary images. The registration is preferably carried out using the modulation that has been extracted. Here, the modulation that has been extracted is combined with the image data in the same temporal resolution. To this end, typically the at least two binary images that differ from one another in the fourth dimension are broadly brought aligned with one another, taking local distortions into account by means of elastic models. A combination of the at least two binary images with the image data that have an identical temporal resolution can be advantageous, since further orientation points can be used for the registration. Significant pixels in the image data can be used for the elastic registration of the modulation that has been extracted. Typically, the registration is carried out in an iterative manner. By the elastic registration, the temporal motion of individual pixels can be determined and/or quantified. As a result, the characteristic of the organ can be determined in a particularly precise manner. Slight and/or local changes in the organ can be detected.

In another embodiment of the method, the sub-visual tagging in the image space includes at least one of the following modulations for at least one point in time:
  reduction of the signal intensity along a grid structure,
  reduction of the signal intensity along at least one axis,
  linear change in a signal intensity of the image data in at least one direction,
  radial change in a signal intensity of the image data emanating from at least one pixel.

As noted, magnetic resonance data are typically in the frequency domain. The frequency domain is linked to the image domain by a Fourier transformation. If magnetic resonance data are reconstructed into image data, the Fourier transformation converts the data from the frequency domain to the image domain. In the image domain, the tagging pattern preferably corresponds with at least one point of time in the aforementioned modulations. If the tag is extracted from the image data, then it will correspond with the tagging pattern and consequently with one of the aforementioned modulations. The extraction of the tag may also ensue from the magnetic resonance data available in the frequency domain. In the frequency domain, the tag typically generates a modulation that differs from the aforementioned modulations.

Typically, the tagging pattern is imprinted on the spins during the execution of the magnetic resonance sequence. The tagging pattern preferably generates a spatial modulation during the execution of the tagging module as above. Motion in the examination region and/or in the organ typically leads to a deformation of the tagging pattern. Due to the sub-visual characteristic of the tag, the reduction and/or change in the signal intensity of the modulation is typically a maximum of 50%, preferably a maximum of 30%, particularly preferably a maximum of 15%, of the highest contrast in the sub-visually tagged image data.

If a linear change in the signal intensity of the image data is used for tagging, then the image data in one spatial direction represent a gradient of the signal intensity. The gradient is typically superimposed on the clinical contrast of the examination region. Such a tagging pattern is typically particularly subtle and is difficult for the human eye to detect. Consequently, where there is a linear change in the signal intensity, a sub-visual display of the tagging pattern is achieved in a particularly effective manner. Deformations of the organ into this one spatial direction are typically easy to detect.

If a grid structure is used as a tagging pattern, then deformations of the organ into all the spatial directions included in the grid structure can be detected. Furthermore, the rectangular structure of the grid typically allows a particularly precise determination of the characteristic of the organ. If a reduction in the signal intensity along at least one axis is generated by the tagging module, then the line described by the axis can be aligned with the organ in a flexible manner. Likewise, a number of axes in respective spatial directions, optionally with intersect points, can be used as the tagging pattern. As a result, distortions of the organ into the various spatial directions can be detected and the characteristic of the organ can be determined in a particularly precise manner.

Further tagging patterns not mentioned explicitly may be used. It is also possible for a number of tagging patterns to be combined. The method according to the invention can also be carried out repeatedly with different tagging patterns. As a result thereof, the precision of the determination of the characteristic of the organ can be increased.

In an embodiment of the method, the tagging module has an RF pulse, which RF pulse generates a tagging flip angle that is smaller than 90°, in particular smaller than 60°, preferably smaller than 45°, and most preferably smaller than 30°.

The tagging module typically generates a location-dependent modulation of the spins, with the spins being prepared in certain spatial positions. These spatial positions preferably reflect the tagging pattern. The preparation is typically intended to generate a reduction in the signal from the spins that have been excited in the magnetic resonance data that is to be acquired. To this end, the spins are typically skewed by a defined angle toward their equilibrium position, the vertical, by an RF pulse, which is included in the tagging module. The defined angle can be referred to as the tagging flip angle. The greater the tagging flip angle, the lower is the magnetization in the vertical caused by the spins and the fainter is the signal generated by a subsequent block in the region modulated by the tagging module. The smaller the tagging flip angle, the less intensively the signal is typically reduced and/or modulated. The use of small tagging flip angles can consequently be applied to sub-visual tagging. The degree of intensity of tagging may be changed through the selection of the tagging flip angle. In particular, a tagging pattern that is not detectable to the naked eye, in particular without any contrast-enhancing measures, can be generated. The tagging pattern may be selected such that it is not visible to a radiologist in the sub-visually tagged image data and can be used for the determination of the characteristic of the organ.

In another embodiment of the method, a function of the organ is determined on the basis of the magnetic resonance data independently from the sub-visual tagging.

Preferably, a function of the organ can be determined on the basis of the sub-visually tagged image data, but a tag is preferably not required for determining the function of the organ. The sub-visual tagging preferably does not affect the quality of the magnetic resonance data used for the determination of the function. If the magnetic resonance sequence were to be executed without a tagging module and magnetic resonance data were to be acquired, on the basis of which magnetic resonance data the function of the organ would be determined, then the result that ensued would not differ from the result that would be determined on the basis of the sub-visually tagged magnetic resonance data. The function of the organ is preferably determined on the basis of the image data. Depending on the function that is to be determined, a specific contrast may be required for the image data, which contrast may be selected for example, when selecting the first magnetic resonance sequence. For determining the function, image-processing methods such as a free-form deformation can be used. The characteristic of the organ that has been determined by the method according to the invention can be taken into account when determining the function of the organ. If the characteristic of the organ is a deformation, for example, then different states of deformation of the organ can be considered when determining the function of the organ. If the organ is a heart for example, then on the basis of the characteristic of the organ, the point of time of diastole and/or of systole can be taken into account when determining the function of the organ.

An advantage of this embodiment of the method is that, after executing the magnetic resonance sequence, magnetic resonance data are available that can be used for determining a characteristic of the organ and for determining a function of the organ. The magnetic resonance data are preferably acquired such that the quality of the function that has been determined is not affected by the sub-visual tag. The magnetic resonance data are preferably acquired such that the quality of the characteristic that has been determined on the basis of the tag is not affected by the sub-visual tagging. With this embodiment of the method, comprehensive findings relating to the organ can be determined with only one scan.

In another embodiment of the method, in further process steps, the magnetic resonance data are reconstructed into image data, and on the basis of the image data, the function of the organ is determined.

On the basis of the image data, at least one function of the organ is preferably determined. This typically involves at least one quantitative value that characterizes the function of the organ being determined. For example, a ventricular function of the heart can be characterized on the basis of a temporal course of the volume of a ventricle. In addition to this, further quantitative values, such as the mass and/or a contraction rate of the organ, can be measured and used for the determination of the function of the organ, in particular of the heart. An advantage of this embodiment of the method is that comprehensive information about the organ can be obtained with only one scan. Both the characteristic and the function of the organ can be determined accurately.

In another embodiment of the method, the organ is a heart and the function of the organ is determined by a scan designed to show at least one of the volume of the heart and/or the volume of a partial region of the heart, stroke volume, cardiac mass, or ejection fraction. The scans carried out are characteristic of the function of a heart and can be used in an analysis of the health thereof and/or of possible disease. In particular, the end-systolic and/or the diastolic volume of the heart can be determined on the basis of the temporally resolved magnetic resonance data.

For example, if the magnetic resonance data are reconstructed into image data in a further process step, then the image data can be segmented such that the cardiac wall and/or the boundary thereof can be determined. From this, a function of the heart can be determined. In addition, on the basis of the magnetic resonance data, a characteristic, in particular a deformation of the heart, in particular of the heart muscle, can be determined, since a tagging pattern has preferably been imprinted on the heart muscle and in particular on the region encompassed by the heart muscle.

In another embodiment of the method, the characteristic of the organ is a periodic deformation of the organ. The method according to the invention allows the determination of a characteristic of the organ, which characteristic undergoes a temporal change. The periodic deformation of an organ occurs due to respiration and/or blood flow. The organ typically exhibits a motion that is repeated after an interval. The motion can occur actively and/or passively. The periodic deformation may be a periodic motion of the entire organ, for example, a translation and/or a rotation. Typically, the periodic deformation of the organ includes local changes in partial regions (sub-regions) of the organ and/or in the sheath that envelops the organ. Such periodic deformations can be detected using the method according to the invention.

During the execution of the magnetic resonance sequence, the temporal resolution of the magnetic resonance data and of the image data typically can be freely selected. If the periodic deformation of an organ is to be determined, then a temporal resolution of the image data that are to be reconstructed from the magnetic resonance data is preferably greater than the duration of a period. The higher the temporal resolution of the image data, the more precisely can the characteristic of the organ typically be determined. If a periodic deformation of the organ is determined using the method according to the invention, then, when using sub-visual tagging, a function of the organ can additionally be determined and/or the magnetic resonance data can be reconstructed into image data that depicts anatomy.

In another embodiment of the method, the organ is a heart. The heart undergoes a periodic motion. To characterize the health of the heart, a determination of the periodic motion and/or a determination of a function, such as the stroke volume thereof, are particularly advantageous.

In an embodiment of the method, the magnetic resonance sequence is based on a LISA-SSFP sequence. SSFP sequences have a strong contrast between the blood and the myocardium, as a result of which the myocardium can be clearly differentiated from the area surrounding it. In cardiac examinations, a function of the heart, such as the ventricular volume can be determined with particular precision. For this purpose, typically a temporally resolved SSFP-sequence, such as a cine SSFP sequence, is typically used. Deformations, in particular local deformations, can only be detected imprecisely using the cine SSFP sequence. The LISA-SSFP sequence combines a tagging module with the cine SSFP sequence. The pattern generated by the tagging module in a cine SSFP sequence impairs the contrast in the image data that reproduces the anatomy. As a result, the function of the organ cannot be determined or only determined imprecisely. For example, due to the tagging pattern, it can be more difficult to distinguish the heart muscle tissue from the ventricular blood and from the tissue surrounding the ventricle. According to this embodiment of the method, the LISA-SSFP sequence has a tagging module for sub-visual tagging.

An advantage of this embodiment of the method is that, by using this magnetic resonance sequence, both the function of the heart and the periodic deformation can be determined in a particularly precise manner. As a result, the method is particularly efficient, in particular in terms of duration of the scan and costs. The method preferably allows the scanning of local deformations of the organ. In particular, compared with using a cine SSFP sequence not only can relative changes in length, but also absolute and/or regional deformations can be detected. Thus, for example, local deformations of the myocardium can be detected, which is necessary for the diagnosis of ischemia. Furthermore, motions of the sheath that envelops the organ can be detected.

Compared with tagging methods that are based on gradient echo sequences, the cine-SSFP-sequence is able to achieve a higher temporal and spatial resolution. A LISA-SSFP sequence with sub-visual tagging can generate the results of a tagged gradient echo sequence and a cine-SSFP-sequence combined. As a result, the acquisition time is shortened and/or the patient has to hold his or her breath less frequently and/or for a shorter period. The magnetic resonance data that are used to analyze the motion and/or deformation can at the same time be used to determine a function of the organ and be reconstructed into image data that represents the anatomy of the organ.

Furthermore, the invention encompasses a magnetic resonance apparatus with a control computer. The control computer is designed to carry out the method according to the invention for determination of a characteristic of an organ. For this purpose, the control computer has an execution processor, a determination processor, and a core processor with an input unit and an output unit.

The execution processor is designed to execute the magnetic resonance sequence, for acquisition of temporally resolved magnetic resonance data of the organ. The magnetic resonance data can be provided to the control computer by the input unit and an algorithm for carrying out the method according to the invention can optionally be provided. Further functions, algorithms, or parameters required in the method can be provided to the control computer and/or the determination processor via the input unit.

The determination processor is designed to determine the characteristic of the organ using the sub-visual tag. The method according to the invention is carried out by algorithms that can be executed in the core processor. The characteristic and/or further results of an embodiment of the method according to the invention, such as the function of the organ and/or image data, can be provided via the output unit. The control computer and/or the determination processor can be incorporated into the magnetic resonance apparatus. The control computer and/or the determination processor can also be installed separate from the magnetic resonance apparatus. The control computer and/or the determination processor can be connected to the magnetic resonance apparatus.

Embodiments of the magnetic resonance apparatus according to the invention are analogous to the embodiments of the method according to the invention. The magnetic resonance apparatus may have further components that are necessary and/or advantageous to carry out the method according to the invention. The magnetic resonance apparatus can also be designed to transmit control signals and/or to receive and/or process control signals, in order to carry out the method according to the invention. The determination processor is preferably part of the control computer of the magnetic resonance apparatus according to the invention. In a memory of the control computer, computer programs and further software can be stored, with which the core processor automatically controls and/or implements the method according to the invention.

The present invention also encompasses a non-transitory, computer-readable data storage medium encoded with programming instructions that, when the storage medium is loaded into a control computer or computer system of a magnetic resonance imaging apparatus, cause the computer or computer system to operate the magnetic resonance imaging apparatus in order to implement any or all of the embodiments of the inventive method, as described above. Examples of electronically readable data carriers are a DVD, a magnetic tape or a USB stick, on which electronically readable control data, in particular software, is stored.

Advantages of the magnetic resonance apparatus according to the invention and the computer readable data carrier according to the invention essentially correspond to the advantages of the method according to the invention for determining a characteristic of an organ, as described in detail above.

DESCRIPTION OF THE PREFERRED EMBODIMENTS

Figure 1:
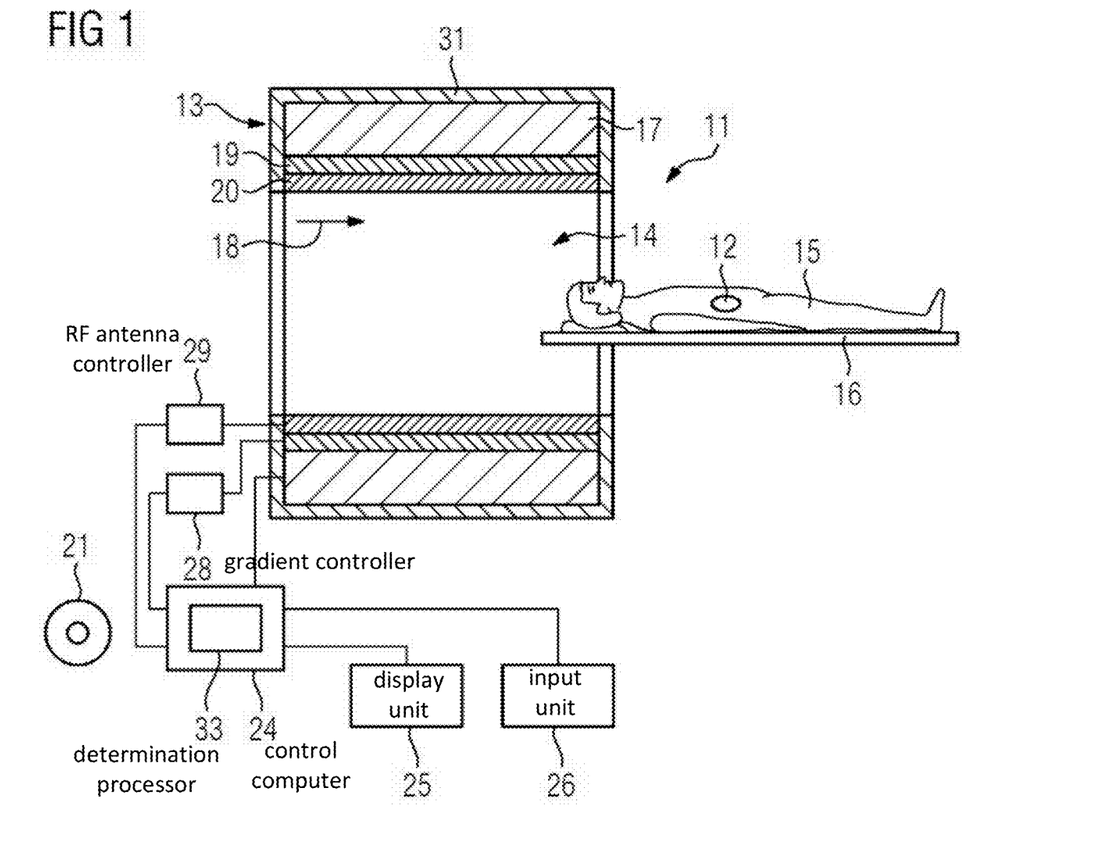
FIG. 1 schematically illustrates a magnetic resonance apparatus according to the invention.

FIG. 1 schematically shows a magnetic resonance apparatus 11 according to the invention for implementing the method according to the invention. The magnetic resonance apparatus 11 has a scanner 13 with a basic field magnet 17 that generates a strong and constant basic magnetic field 18. The scanner 13 has a cylindrical patient accommodation area 14 to accommodate a patient 15. The patient accommodation area 14 is cylindrically surrounded in a circumferential direction by the scanner 13. The patient 15, who has an organ 12, can be moved by a patient-positioning device 16 into the patient accommodation area 14. The patient-positioning device 16 for this purpose has a patient bed that is moveably arranged inside the scanner 13. The scanner 13 is protected externally by a housing cover 31.

The scanner 13 further has a gradient coil arrangement 19, for spatially encoding magnetic resonance signals during an imaging process. The gradient coil arrangement 19 is controlled by a gradient controller 28. Furthermore, the scanner 13 has a radio-frequency antenna 20, which, in the embodiment shown, is configured as a body coil that is fixedly incorporated into the scanner 13, and a radio-frequency antenna controller 29. The radio-frequency antenna 20 is controlled by the radio-frequency antenna controller 29 so as to emit radio-frequency pulses into an examination area essentially formed by the patient accommodation area 14. The radio-frequency pulses deflect the magnetization of nuclear spins in the patient 15 that have been excited to resonance by the radio-frequency pulses, with respect to the magnetic field lines of the basic magnetic field 18. As those deflected nuclei return to the steady state, they emit the aforementioned magnetic resonance signals. The magnetic resonance signals can be detected by the same, or a different, antenna from which the excitation pulses were radiated.

To control the basic field magnet 17, the gradient controller 28 and the radio-frequency antenna controller 29, the magnetic resonance apparatus 11 has a control computer 24. The control computer 24 centrally controls the magnetic resonance apparatus 11, by executing MR control sequences. Control data, such as imaging parameters, and reconstructed image data, can be displayed to a user on a display unit 25, for example, on at least one monitor of the magnetic resonance apparatus 11. In addition, the magnetic resonance apparatus 11 has an input unit 26, via which data and/or imaging parameters can be entered by a user during a scanning procedure. The control computer 24 can encompass the gradient controller 28 and/or the radio-frequency antenna controller 29 and/or the display unit 25 and/or the input unit 26. The control computer 24 further includes a determination processor 33. The magnetic resonance apparatus 11 is consequently configured with the determination processor 33 to implement a determination according to the method of the invention.

The magnetic resonance apparatus 11 that is shown, may of course include further components that magnetic resonance apparatuses usually have. The general manner of operation of a magnetic resonance apparatus is known to those skilled in the art, such that a more detailed description is not necessary herein.

The method according to the invention can be embodied as program code stored in a non-transitory, computer-readable data storage medium 21. The electronically readable program code causes the control computer 24 to operate the magnetic resonance apparatus 11 in order to implement the inventive method when the data 21 is loaded into the control computer 24.

Figure 2:
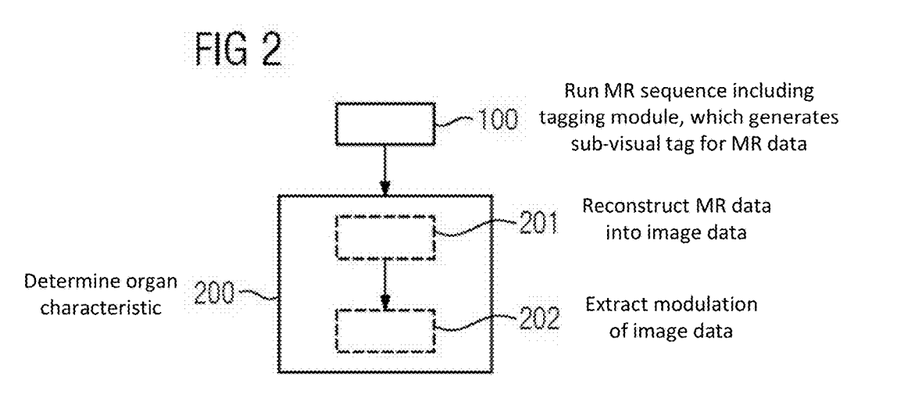
FIG. 2 is a flowchart for a first embodiment of the method according to the invention.

FIG. 2 shows a flowchart of a first embodiment of the method according to the invention. The method used for determining a characteristic of an organ 12 using a magnetic resonance apparatus 11 includes the following process steps: First, in process step 100, a magnetic resonance sequence is run to acquire temporally resolved magnetic resonance data relating to the organ 12. The magnetic resonance sequence includes at least one tagging module, which generates a sub-visual tag for the magnetic resonance data. In process step 200, the determination of the characteristic of the organ 12 ensues, using the sub-visual tag.

Process step 200 can optionally include sub-steps 201 and 202. In sub-step 201, the magnetic resonance data are reconstructed into image data. In sub-step 202, the modulation of the image data that has been generated by the sub-visual tag is extracted. The modulation typically changes as the image data evolves over time and can be used to determine a characteristic of the organ 12. Determining the characteristic of the organ 12 preferably includes an elastic registration based on the modulation that has been extracted. For example, the characteristic of the organ 12 can be a spatial deformation of the organ 12 over time.

Figure 3:
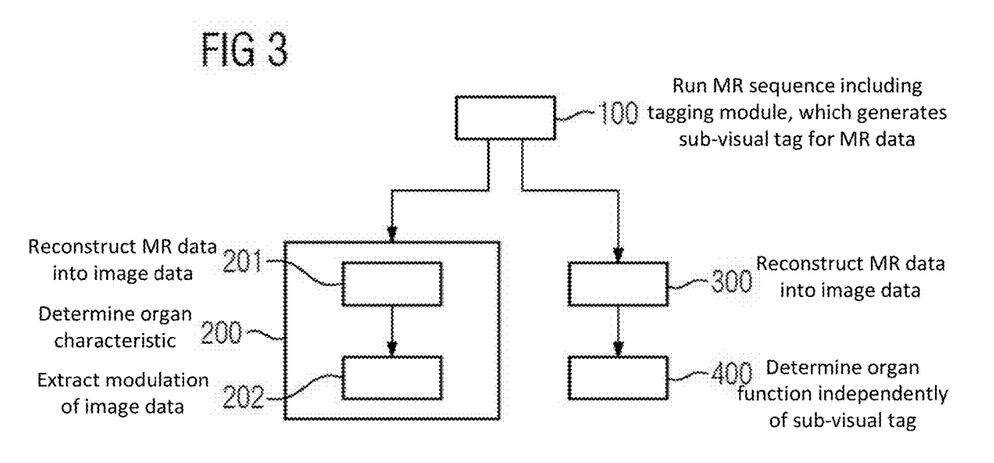
FIG. 3 is a flowchart for a second embodiment of the method according to the invention.

FIG. 3 shows a flowchart of a second embodiment of the method according to the invention. In this embodiment, in process step 100, a magnetic resonance sequence based on a LISA-SSFP sequence and including a tagging module for sub-visual tagging, is executed. This generates magnetic resonance data that are sub-visually tagged. The tag is preferably designed such that the signal intensity along a grid structure is reduced for at least one point in time in the magnetic resonance data that are to be reconstructed into image data. For this purpose, preferably while the patient is in the process of holding his or her breath, two consecutive magnetic resonance sequences are executed, inducing in the examination region tagging lines that are orthogonal to each other.

On the basis of the sub-visual tag, the characteristic of the organ 12 is determined in process step 200. For this purpose, the magnetic resonance data are reconstructed into image data in sub-step 201. The image data can be transmitted to a computation unit, which is optionally not included in the magnetic resonance apparatus 11. In process step 202, the tag lines are preferably combined in an image by a pixel-level minimization method through which temporally resolved tagged images are generated. In the tag images, the endocardial and epicardial contours of the myocardium can be distinguished from each other. A temporal deformation of the myocardium can be determined on the basis of an elastic registration.

In process step 300, the magnetic resonance data are reconstructed into image data. If process step 201 is carried out, sub-step 201 can replace process step 300, or vice versa. On the basis of the image data, a function of the organ 12 is determined in process step 400, the function of the organ 12 preferably being determined independently of the sub-visual tag. Accordingly, the determination of the function is preferably not influenced by the tagging module in the magnetic resonance sequence.

If the organ 12 is a heart, then the function is determined using at least one of the following parameters: the volume of the heart and/or of a partial region of the heart, the stroke volume, the cardiac mass and/or the ejection fraction.

Figure 4:
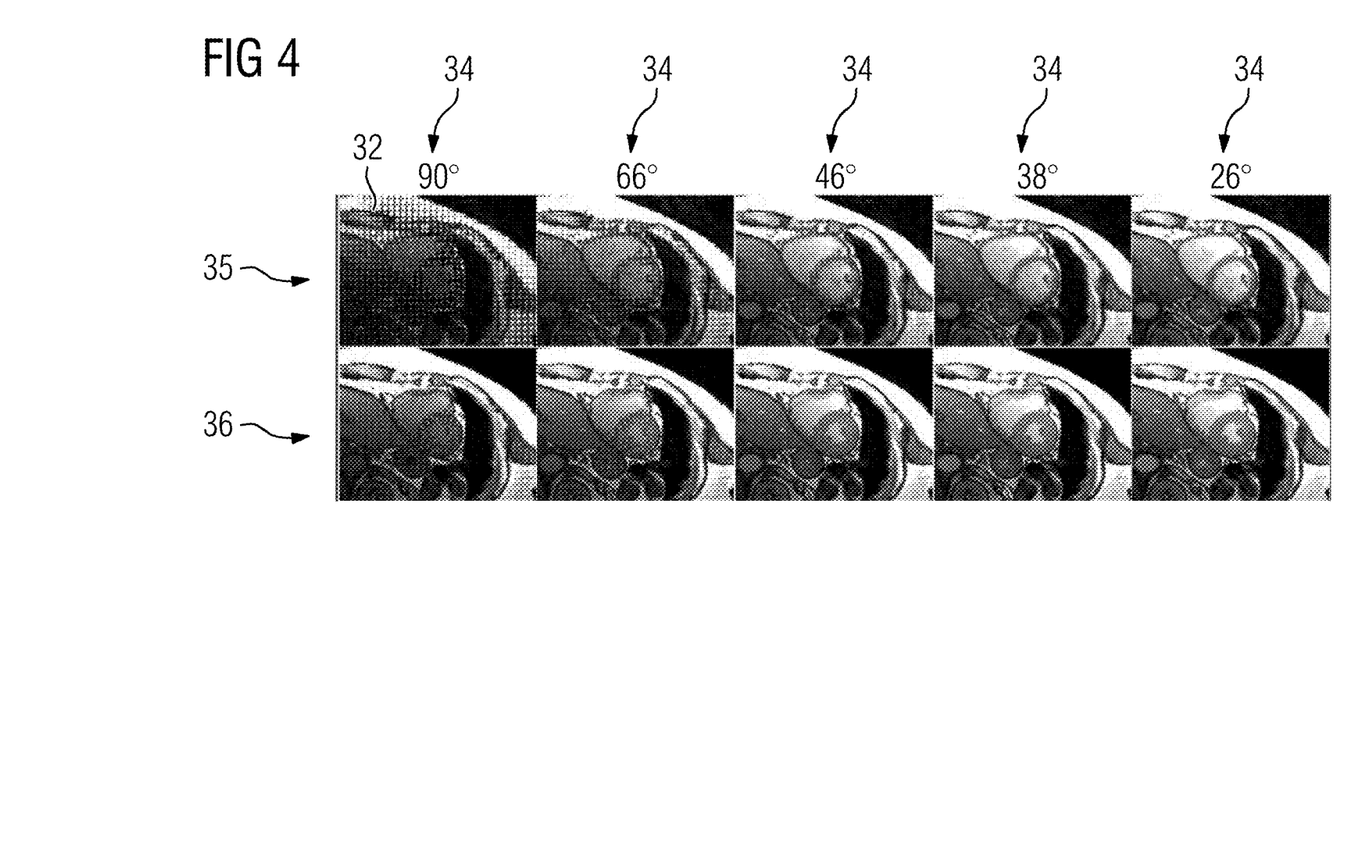
FIG. 4 shows image data that have been acquired using a magnetic resonance sequence that includes a tagging module with various tagging flip angles.

FIG. 4 shows image data that have been acquired using a magnetic resonance sequence that includes a tagging module with various tagging flip angles 34. Here the tagged magnetic resonance data have been reconstructed into tagged image data. The angles shown depict the tagging flip angles 34, used by the RF pulse that is included in the tagging module to excite the spins, and the tagging flip angles 34 relate to the image data shown under the tagging flip angles 34. The image data represent, as the organ 12, a heart at two different times, end-diastole 35 and end-systole 36. The heart undergoes a periodic deformation, which can be shown by temporally resolved acquisition of the magnetic resonance data and temporally resolved generation of image data at different times 35, 36 within a period. The acquisition of the magnetic resonance data typically extends over a number of periods. By extracting the tagging pattern 32, the deformation can be quantified by, for example, the absolute local motion of a position on the surface of the myocardium being determined in a temporally resolved manner in the measurement of length.

A grid structure is used as a tagging pattern 32. The smaller the tagging flip angle 34, the less detectable is the grid structure in the image data. Likewise, the tagging pattern 32 in the image data can be detected more clearly at the time of end-diastole 35 than at the time of end-systole 36. According to one embodiment of the method according to the invention, the tagging module comprises an HF pulse that generates a tagging flip angle 34 that is smaller than 90°, in particular smaller than 60°, in particular smaller than 45°, in particular smaller than 30°. In the image data that has been acquired with the tagging flip angle 34 of 26°, the tagging pattern 32 is not detectable to the naked eye and/or does not impair the contrast created by the anatomy. Accordingly, the tagging pattern 32 is sub-visual in this case.

Equally conceivable tagging patterns 32 are
- a reduction in signal intensity along at least one axis in the image data,
- a linear change in signal intensity of the image data along at least one direction,
- a radial change in signal intensity of the image data emanating from at least one pixel.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for determining a characteristic of an organ of a patient, comprising:
    operating a magnetic resonance (MR) data acquisition scanner, while the patient, having the organ therein, is situated in the MR data acquisition scanner, in order to execute an MR data acquisition sequence so as to acquire temporally resolved MR data relating to the organ, wherein the MR data acquisition sequence is a Linearly Increasing Startup Angles—Steady-State Free Precession (LISA-SSFP) sequence;
    operating said MR data acquisition scanner to execute said MR data acquisition sequence so as to include acquisition of a tagging module that, when an image of the organ is reconstructed from the MR data, produces a sub-visual tag in the reconstructed image, wherein a signal difference in the reconstructed image due to the sub-visual tag is lower than 15% of a maximum signal difference in the reconstructed image; and
    in a computer reconstructing said reconstructed image from the MR data so as to include said sub-visual tag in the reconstructed image, and determining the characteristic of the organ using an electronic signal representing the sub-visual tag in the reconstructed image, and making the determined characteristic available from the computer.

2. A method as claimed in claim 1 comprising, in a processor of the computer provided with image data of said reconstructed image, determining said characteristic of the organ by extracting a modulation, produced by said sub-visual tag, from said image data.

3. A method as claimed in claim 2 comprising, in said processor, executing an elastic registration based on said modulation that has been extracted.

4. A method as claimed in claim 3 comprising, in said processor, using, as said modulation produced by said sub-visual tag, a modulation of said image data selected from the group consisting of reduction of a signal intensity of the image data along a grid structure, reduction of a signal intensity of the image data along at least one axis, a linear change in a signal intensity of the image data in at least one direction, and a radial change in a signal intensity of the image data emanating from at least one pixel of the image data.

5. A method as claimed in claim 1 comprising using, as said characteristic of the organ, a periodic deformation of the organ.

6. A method as claimed in claim 1 comprising operating said MR data acquisition sequence to include, as said tagging module, radiation of a radio frequency (RF) pulse that produces a tagging flip angle of nuclear spins in said organ that is less than 60 degrees.

7. A method as claimed in claim 6 wherein the organ is a heart of the patient, and comprising determining the function of the organ by at least one parameter selected from the group consisting of a volume of the heart, a volume of a sub-region of the heart, a stroke volume of the heart, a cardiac mass of the heart, and an ejection fraction of the heart.

8. A method as claimed in claim 1 comprising operating said MR data acquisition sequence to include, as said tagging module, radiation of a radio frequency (RF) pulse that produces a tagging flip angle of nuclear spins in said organ that is less than 45 degrees.

9. A method as claimed in claim 1 comprising operating said MR data acquisition sequence to include, as said tagging module, radiation of a radio frequency (RF) pulse that produces a tagging flip angle of nuclear spins in said organ that is less than 30 degrees.

10. A method as claimed in claim 1 comprising determining a function of the organ from said MR data independently of said sub-visual tagging.

11. A magnetic resonance (MR) apparatus comprising:
an MR data acquisition scanner;
a computer configured to operate said MR data acquisition scanner, while a patient, having an organ therein, is situated in the MR data acquisition scanner, in order to execute an MR data acquisition sequence so as to acquire temporally resolved MR data relating to the organ, wherein the MR data acquisition sequence is a Linearly Increasing Startup Angles—Steady-State Free Precession (LISA-SSFP) sequence;
said computer being configured to operate said MR data acquisition scanner to execute said MR data acquisition sequence so as to include acquisition of a tagging module that, when an image of the organ is reconstructed from the MR data, produces a sub-visual tag in the reconstructed image, wherein a signal difference in the reconstructed image due to the sub-visual tag is lower than 15% of a maximum signal difference in the reconstructed image; and
said computer being configured to reconstruct said reconstructed image from the MR data so as to include said sub-visual tag in the reconstructed image, and to determine a characteristic of the organ using the sub-visual tag in the reconstructed image, and to make an electronic signal representing the determined characteristic available from the computer.

12. An MR apparatus as claimed in claim 11 wherein said computer is further configured to determine a function of the organ from said MR data independently of said sub-visual tagging.

13. A non-transitory, computer-readable data storage medium encoded with programming instructions, said storage medium being loaded into a computer system of a magnetic resonance (MR) apparatus comprising an MR data acquisition scanner, and said programming instructions causing said computer system to:
operate a magnetic resonance (MR) data acquisition scanner, while a patient, having an organ therein, is situated in the MR data acquisition scanner, in order to execute an MR data acquisition sequence so as to acquire temporally resolved MR data relating to the organ, wherein the MR data acquisition sequence is a Linearly Increasing Startup Angles—Steady-State Free Precession (LISA-SSFP) sequence;
operate said MR data acquisition scanner to execute said MR data acquisition sequence so as to include acquisition of a tagging module that, when an image of the organ is reconstructed from the MR data, produces a sub-visual tag in the reconstructed image, wherein a signal difference in the reconstructed image due to the sub-visual tag is lower than 15% of a maximum signal difference in the reconstructed image; and
reconstruct said reconstructed image from the MR data so as to include said sub-visual tag in the reconstructed image, and determine a characteristic of the organ using the sub-visual tag in the reconstructed image, and make an electronic signal representing the determined characteristic available from the computer.

14. A non-transitory, computer-readable data storage medium as claimed in claim 13 wherein said programming instructions further cause said computer system to determine a function of the organ from said MR data independently of said sub-visual tagging.

* * * * *